US00PP24226P2

(12) United States Plant Patent
Wezelenburg

(10) Patent No.: US PP24,226 P2
(45) Date of Patent: Feb. 11, 2014

(54) ***GINKGO* TREE NAMED 'MENHIR'**

(50) Latin Name: *Ginkgo biloba*
Varietal Denomination: Menhir

(71) Applicant: Jan-Willem Wezelenburg, Hazerswoude (NL)

(72) Inventor: Jan-Willem Wezelenburg, Hazerswoude (NL)

( * ) Notice: Subject to any disclaimer, the term of this patent is extended or adjusted under 35 U.S.C. 154(b) by 0 days.

(21) Appl. No.: 13/694,945

(22) Filed: Jan. 22, 2013

(51) Int. Cl.
*A01H 5/00* (2006.01)

(52) U.S. Cl.
USPC ..... Plt./216

(58) Field of Classification Search
USPC ..... Plt./216
See application file for complete search history.

(56) References Cited

PUBLICATIONS

PLUTO UPOV-Plant Variety Database 2013/01, retrieved from the internet on Jun. 6, 2013 at <https://www3.wipo.int/pluto/user/en/index.jsp> PBR 20101236, published Aug. 15, 2010. pp. 3.*
Langthorns plantery 2013, retrieved from the internet on Jun. 17, 2013 at <http://new.langthorns.com/index.php?route=product/product&product_id=2047>, pp. 1.*

* cited by examiner

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of *Ginkgo*, 'Menhir', that is characterized by its narrowly upright (fastigiated) plant habit, its dense branching, its good response to transplanting with little growth loss after transplanting, and its leaves that are dark green in color with a glaucous coating.

2 Drawing Sheets

Botanical classification: *Ginkgo biloba.*
Variety denomination: 'Menhir'.

BACKGROUND OF THE INVENTION

The present invention relates to a new and distinct cultivar of *Ginkgo biloba* and will be referred to hereafter by its cultivar name, 'Menhir'. 'Menhir' is a new cultivar of *Ginkgo* tree grown for use as a landscape plant.

The Inventor discovered the new cultivar, 'Menhir' as a naturally occurring whole plant mutation in a seedbed at his nursery in Hazerswoude, The Netherlands in summer of 1996. The seedbed had been planted with seeds collected from an unnamed open pollinated plant of *Ginkgo biloba.*

Asexual propagation of the new cultivar was first accomplished by grafting by the Inventor in Hazerswoude, The Netherlands in 1998. Asexual propagation of the new cultivar by grafting has been determined that the characteristics are stable and are reproduced true to type in successive generations.

SUMMARY OF THE INVENTION

The following traits have been repeatedly observed and represent the characteristics of the new cultivar as grown outdoors in Hazerswoude, The Netherlands. These attributes in combination distinguish 'Menhir' as a unique cultivar of *Ginkgo.*

1. 'Menhir' exhibits a narrowly upright (fastigiated) plant habit.
2. 'Menhir' exhibits dense branching.
3. 'Menhir' responds very well to transplanting with little growth loss after transplanting.

4. 'Menhir' exhibits leaves that are dark green in color with a glaucous coating.

The seed parent, an unnamed plant of *Ginkgo biloba*, differs from 'Menhir' in having a wider plant habit and in having dark green leaves that lack a glaucous coating. 'Menhir' can be most closely compared to the cultivars 'Tit' (not patented) and 'Fastigiata' (not patented). Both are similar to 'Menhir' in having upright plant habits. Both differ from 'Menhir' in having looser and less branched plant habits, in having leaves that lack a glaucous coating, and in exhibiting growth problems the first year after transplanting.

BRIEF DESCRIPTION OF THE DRAWING

The accompanying colored photographs illustrates the overall appearance and distinct characteristics of the new 'Menhir'. The photographs were taken of a 2.5 year-old plant of 'Menhir' as grown outdoors in a 10-liter container in Hazerswoude, The Netherlands.

The photograph in FIG. 1 provides a view of the plant habit of 'Menhir'.

Figure 1:
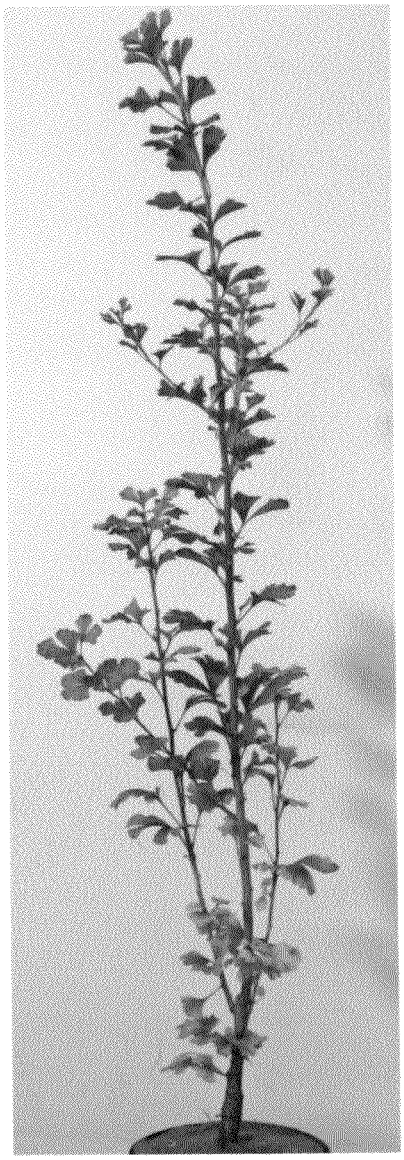
Figure 2:
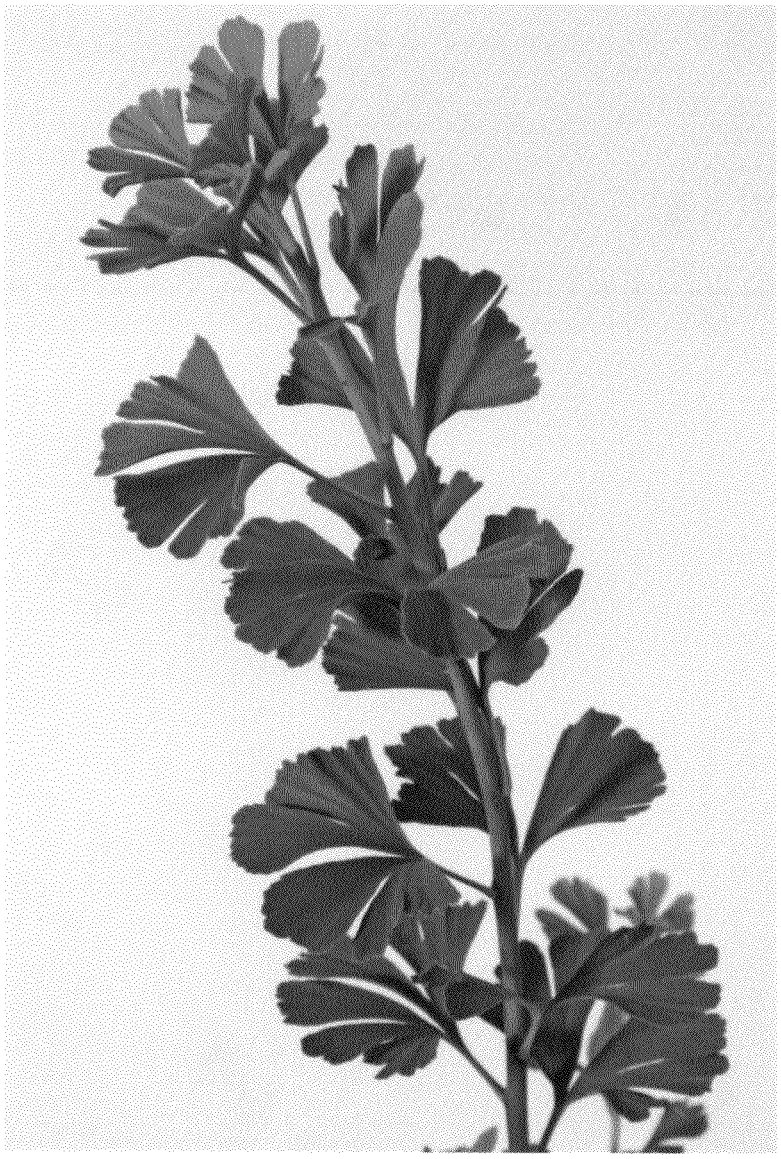

The photograph in FIG. 2 provides a close-up view of the foliage of 'Menhir'.

The colors in the photograph are as close as possible with the digital photography techniques available, the color values cited in the detailed botanical description accurately describe the colors of the new 'Menhir'.

DETAILED BOTANICAL DESCRIPTION

The following is a detailed description of 2.5 year-old trees of the new cultivar as field grown outdoors in October in Hazerswoude, The Netherlands. Plants were grown under average day temperatures of 12° to 30° C. and average night temperatures of 4° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Flowers have not been observed to date, it may take many years of growth before it blooms or not bloom at all.

*Plant type.*—Deciduous tree.

*Plant habit.*—Narrowly upright; fastigiated, densely branched.

*Height and spread.*—Has been observed to reach about 131 cm in height and about 31 cm in width when 2.5 years in age, up to 5 m in height and 1 m in width when mature in the landscape.

*Cold hardiness.*—At least in U.S.D.A. Zone 3.

*Diseases.*—Have been observed to be disease free (typical for plants of *Ginkgo biloba*).

*Root description.*—Fibrous, freely branched.

*Propagation.*—Grafting.

*Growth rate.*—Moderate to highly vigorous, responds well to transplanting with good growth the first year after transplanting (not typical for plants *Ginkgo biloba*).

Stem description:

*Shape.*—Rounded.

*Stem color.*—New growth N144A, mature wood; N199C.

*Stem size.*—Average lateral branch length is 30.3 cm in length and 3 mm in diameter.

*Stem surface.*—Smooth and dull.

*Stem strength.*—Very strong.

*Branching habit.*—Average of 7 lateral branches.

Foliage description:

*Leaf shape.*—Flabellate and slightly convex.

*Leaf division.*—Simple.

*Leaf base.*—Attenuate.

*Leaf apex.*—Cleft.

*Leaf fragrance.*—None.

*Leaf venation.*—Parallel, upper surface 137A, lower surface; 137B to 137C.

*Leaf margins.*—Angulate-incised.

*Leaf arrangement.*—Alternate.

*Leaf attachment.*—Petiolate.

*Leaf buds.*—Bluntly deltoid to broadly conical in shape, an average 3 mm in length and 4 mm in diameter, a blend of 194A and a color between 167A and N199C.

*Leaf surface.*—Smooth and dull on upper and lower surface.

*Leaf size.*—Average of 6.1 cm in length and 6.9 cm in width.

*Leaf color.*—Young leaves upper surface; 144A, young leaves lower surface; 144A to 144B, mature leaves upper surface; 137A with a glaucous coating of 189A, mature leaves lower surface; 137B to 137C, fall upper and lower surface; a color between 8A and 13B.

*Petioles.*—Flattened in shape, average of 2.5 cm in length, 1.5 mm in height, 3 mm in width, color; 143A, becoming 144A at the base.

Flower, fruit, and seed description: Flowers have not been observed to date, it may take many years of growth before it blooms or not bloom at all.

*Fruit and seeds.*—Have not been observed.

It is claimed:

1. A new and distinct cultivar of *Ginkgo* tree named 'Menhir' as herein illustrated and described.

* * * * *